US006835513B2

(12) United States Patent
Jubran et al.

(10) Patent No.: US 6,835,513 B2
(45) Date of Patent: Dec. 28, 2004

(54) CARBAZOLE BASED CHARGE TRANSPORT COMPOUNDS

(75) Inventors: Nusrallah Jubran, St. Paul, MN (US); Zbigniew Tokarski, Woodbury, MN (US); Kam W. Law, Woodbury, MN (US)

(73) Assignee: Samsung Electronic Co., Ltd., Suwon (KR)

( * ) Notice: Subject to any disclaimer, the term of this patent is extended or adjusted under 35 U.S.C. 154(b) by 23 days.

(21) Appl. No.: 10/382,392

(22) Filed: Mar. 6, 2003

(65) Prior Publication Data

US 2003/0207188 A1 Nov. 6, 2003

Related U.S. Application Data

(60) Provisional application No. 60/368,253, filed on Mar. 28, 2002.

(51) Int. Cl.$^7$ .......................... G03G 5/047; G03G 5/05
(52) U.S. Cl. .............................. 430/58.15; 430/58.45; 430/58.6; 430/79; 430/124; 430/117; 548/257; 548/364.7; 548/518; 548/254; 548/440; 548/444; 399/159
(58) Field of Search ....................... 430/79, 58.45, 430/58.6, 124, 117, 257, 58.15; 548/364.7, 518, 254, 440, 444; 399/159

(56) References Cited

U.S. PATENT DOCUMENTS

| 3,932,455 | A | 1/1976 | Bilofsky et al. |
| 3,943,108 | A | 3/1976 | Teuscher |
| 4,072,519 | A | 2/1978 | Pearson et al. |
| 4,297,426 | A | 10/1981 | Sakai et al. |
| 4,322,487 | A | 3/1982 | Merrill et al. |

(List continued on next page.)

FOREIGN PATENT DOCUMENTS

| EP | 1 202 120 A2 | 5/2002 | |
| GB | 1047525 | 11/1966 | |
| JP | 10239875 A | * 9/1998 | ............ G03G/5/06 |
| WO | WO02051905 A1 | * 7/2002 | |

OTHER PUBLICATIONS

Boyd et al., "The Dimerisation of 5–Methylene–$^2$–1,3, 4–oxadiazolines," J. Chem. Soc., C, Organic 12, pp. 2314–2317, 1971.
Atherton et al., "Synthesis of 3(S)–Acylamino–1– [(Phenyl)(1H–Tetrazol–5–yl)Amino]–2–Azetidinones," Tetrahedron, vol. 39, No. 15, pp. 2599–2608, 1983.
Murakami et al., "An Efficient Synthesis of 1,1–Disubstituted Hydrazines," Chem. Pharm. Bull., 31(2), pp. 423–428, 1983.

*Primary Examiner*—Christopher Rodee

(74) *Attorney, Agent, or Firm*—Patterson, Thuente, Skaar & Christensen, P.A.

(57) ABSTRACT

Improved organophotoreceptors have:
 (a) a charge transport compound having the formula:

where $R_1$ is hydrogen, a branched or linear alkyl group, a branched or linear unsaturated hydrocarbon group, an ether group, or an aryl group; and
$R_2$ and $R_3$ independently have a structure of:

in which Ar is selected form the group consisting of;

$R_4$ is a hydrogen, or an aromatic group;
(b) a charge generating compound; and
(c) an electrically conductive substrate.

21 Claims, No Drawings

U.S. PATENT DOCUMENTS

| | | |
|---|---|---|
| 4,426,327 A | 1/1984 | Hashimoto et al. |
| 4,476,137 A | 10/1984 | Haviv et al. |
| 4,786,571 A | 11/1988 | Ueda |
| 4,957,838 A | 9/1990 | Aruga et al. |
| 5,089,366 A * | 2/1992 | Haino et al. ............ 430/58.45 |
| 5,128,227 A | 7/1992 | Monbaliu et al. |
| 5,274,116 A | 12/1993 | Martin et al. |
| 5,932,384 A | 8/1999 | Mitsumori et al. |
| 6,001,522 A | 12/1999 | Woo et al. |
| 6,020,096 A | 2/2000 | Fuller et al. |
| 6,030,734 A | 2/2000 | Mitsumori |
| 6,066,426 A | 5/2000 | Mott et al. |
| 6,099,996 A | 8/2000 | Yanus et al. |
| 6,140,004 A | 10/2000 | Mott et al. |
| 6,214,503 B1 | 4/2001 | Gaidelis et al. |
| 6,340,548 B1 | 1/2002 | Jubran et al. |
| 2002/0064397 A1 | 5/2002 | Kellie et al. |
| 2002/0122997 A1 | 9/2002 | Lee et al. |

* cited by examiner

CARBAZOLE BASED CHARGE TRANSPORT COMPOUNDS

CROSS REFERENCE TO RELATED APPLICATIONS

This application claims priority to U.S. Provisional Patent Application Ser. No. 60/368,253 filed Mar. 28, 2002, now abandoned, to Kam et al., entitled "Electrophotographic Organophotoreceptors With Novel Charge Transport Compounds," incorporated herein by reference.

FIELD OF INVENTION

This invention relates to organophotoreceptors suitable for use in electrophotography and, more specifically, to flexible organophotoreceptors having novel charge transport compounds comprising a diformylcarbazole bishydrazone group.

BACKGROUND

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas. A liquid or solid toner is then deposited in either the charged or uncharged areas depending on the properties of the toner to create a toner image on the surface of the photoconductive layer. The resulting toner image can be transferred to a suitable receiving surface such as paper. The imaging process can be repeated many times to complete a single image and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport compound is to accept at least one type of these charge carriers, generally holes, and transport them through the charge transport layer in order to facilitate discharge of a surface charge on the photoconductive element.

SUMMARY OF THE INVENTION

In a first aspect, the invention features an organophotoreceptor that includes:

(a) a charge transport compound having the formula:

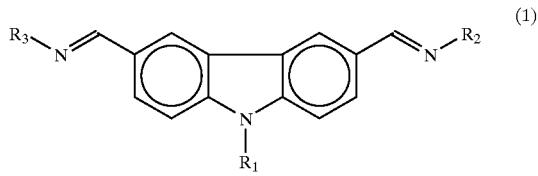

where $R_1$ is hydrogen, a branched or linear alkyl group (e.g., a $C_1$–$C_{30}$ alkyl group), a branched or linear unsaturated hydrocarbon group, an ether group, or an aryl group (e.g., a phenyl or naphthyl group); and $R_2$ and $R_3$ independently have a structure of:

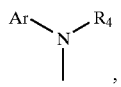

in which Ar is selected form the group consisting of;

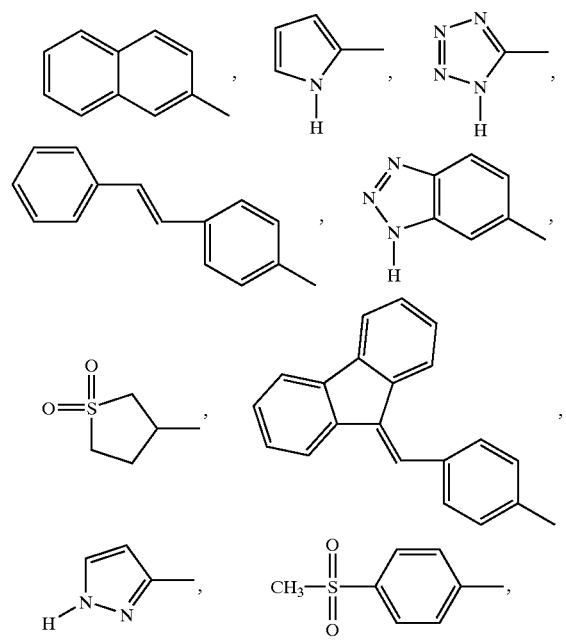

$R_4$ is a hydrogen, or an aromatic group;
(b) a charge generating compound; and
(c) an electrically conductive substrate.

In a second aspect, the invention features an electrophotographic imaging apparatus that includes (a) a plurality of support rollers; and (b) the above-described organophotoreceptor operably connected to the support rollers with motion of the support rollers resulting in motion of the organophotoreceptor. The apparatus can further include, for example, a liquid toner dispenser, although dry toner can also be used with the organophotoreceptor.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a novel charge transport material having the formula (a) a charge transport compound having the formula:

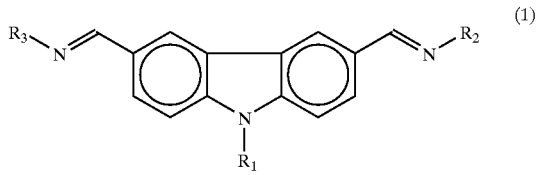

where $R_1$ is hydrogen, a branched or linear alkyl group (e.g., a $C_1$–$C_{20}$ alkyl group), a branched or linear unsaturated hydrocarbon group, an ether group, or an aryl group (e.g., a phenyl or naphthyl group); and $R_2$ and $R_3$ independently have a structure of:

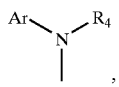

in which Ar is selected form the group consisting of;

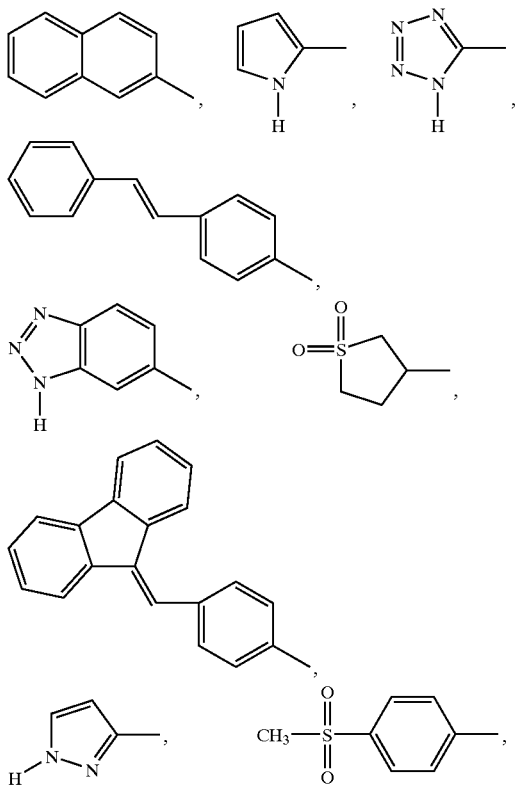

$R_4$ is a hydrogen, or an aromatic group.

These photoreceptors can be used successfully with liquid toners to produce high quality images. The high quality of the images can be maintained after repeated cycling.

Other features and advantages of the invention will be apparent from the following description of the preferred embodiments thereof, and from the claims.

DETAILED DESCRIPTION

Charge transport compounds with desirable properties can be formed having a diformylcarbazole bishydrazone composition or derivatives thereof. These charge transport compounds have desirable properties as evidenced by their performance in organophotoreceptors for electrophotography. The organophotoreceptors are particularly useful in laser printers and the like as well as photocopiers, scanners and other electronic devices based on electrophotography. The use of these charge transport compounds is described below in the context of laser printers use, although their application in other devices operating by electrophotography can be generalized from the discussion below.

To produce high quality images, particularly after multiple cycles, it is desirable for the charge transport compounds to form a homogeneous solution with the polymeric binder and remain approximately homogeneously distributed through the organophotoreceptor material during the cycling of the material. In addition, it is desirable to increase the amount of charge that the charge transport compounds can accept (indicated by a parameter known as the acceptance voltage or "$V_{acc}$"), and to reduce retention of that charge upon discharge (indicated by a parameter known as the residual voltage or "$V_{res}$").

There are many charge transport compounds available for electrophotography. Examples of charge transport materials are pyrazoline derivatives, fluorene derivatives, oxadiazole derivatives, stilbene derivatives, hydrazone derivatives, carbazole hydrazone derivatives, polyvinyl carbazole, polyvinyl pyrene, or polyacenaphthylene. However, there is a need for other charge transport compounds to meet the various requirements of particular electrophotography applications.

In electrophotography applications, a charge generating compound within an organophotoreceptor absorbs light to form electron-hole pairs. These electron-hole pairs can be transported over an appropraite time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compounds described herein are especially effective at transporting charge, and in particular holes from the electron-hole pairs formed by the charge generating compound. In some embodiments, a specific electron transport compound can also be used along with the charge transport compound.

The layer or layers of materials containing the charge generating compound and the charge transport compounds are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport compound can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport compound and a charge generating compound with a polymeric binder.

The organophotoreceptors can be incorporated into an electrophotographic imaging apparatus, such as laser printers. In these devices, an image is formed from a physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

The improved charge transport compounds described herein comprises two hydrazone groups conjugated with a carbozole group. Specifically, the compounds are based on a formula

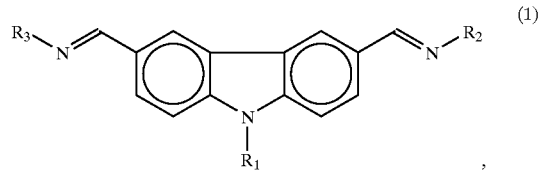

(1)

in which $R_1$ is hydrogen, a branched or linear alkyl group (e.g., a $C_1$–$C_{20}$ alkyl group), a branched or linear unsaturated hydrocarbon group, an ether group, or an aryl group (e.g., a phenyl or naphthyl group), and $R_2$ and $R_3$ each have a nitrogen to form a hydrazone that is bonded to at least one aromatic group. $R_2$ and $R_3$ have independently one of a selected number of specific formulas, as described in detail below. These improved charge transport compounds can be incorporated into corresponding organophotoreceptors.

In describing chemicals by structural formulae and group definitions, certain terms are used in a nomenclature format that is chemically acceptable. The terms groups and moiety have specific meanings. The term group indicates that the generically recited chemical material (e.g., alkyl group, phenyl group, carbazole group, etc.) may have any substituent thereon which is consistent with the bond structure of that group. For example, alkyl group includes alkyl materials such as methyl ethyl, propyl iso-octyl, dodecyl and the like, and also includes such substituted alkyls such as chloromethyl, dibromoethyl, 1,3-dicyanopropyl, 1,3,5-trihydroxyhexyl, 1,3,5-trifluorocyclohexyl, 1-methoxy-dodecyl, phenylpropyl and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, orthocyanophenyl, 1,3, 5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical material is not substituted.

The charge transport compound may or may not be symmetrical. In addition, the above-described formula for the charge transport compound is intended to cover isomers.

Organophotoreceptors

The organophotoreceptor may be, for example, in the form of a plate, a flexible belt, a disk, a rigid drum, or a sheet around a rigid or compliant drum, with flexible belts and rigid drums generally being used in commercial embodiments. The organophoto-receptor may comprise, for example, an electrically conductive substrate and a photoconductive element in the form of one or more layers. The photoconductive element comprises both the charge transport compound and charge generating compound in a polymeric binder, which may or may not be in the same layer. For example, in some embodiments with a single layer construction, the charge transport compound and the charge generating compound are in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer. In the dual layer embodiments, the charge generation layer generally has a thickness form about 0.5 to about 2 microns, and the charge transport layer has a thickness from about 5 to about 35 microns. In a single layer embodiment, the layer with the charge generating compound and the charge transport compound generally has a thickness from about 7 to about 30 microns.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyethylene terepthalate, polyimide, polysulfone, polyethylene naphthalate, polypropylene, nylon, polyester, polycarbonate, polyvinyl fluoride, polystyrene and the like. Specific examples of polymers for supporting substrates included, for example, polyethersulfone (Stabar™ S-100, available from ICI), polyvinyl fluoride (Tedlar®, available from E. I. DuPont de Nemours & Company), polybisphenol-A polycarbonate (Makrofol™, available from Mobay Chemical Company) and amorphous polyethylene terephthalate (Melinar™, available from ICI Americas, Inc.). The electrically conductive materials may be graphite, dispersed carbon black, iodide, conductive polymers such as polypyroles and Calgon conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dye or pigment. Examples of suitable charge generating compounds include metal-free phthalocyanines, metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename Indofast® Double Scarlet, Indofast® Violet Lake B, Indofast® Brilliant Scarlet and Indofast® Orange, quinacridones available from DuPont under the tradename Monastral™ Red, Monastral™ Violet and Monastral™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazopigments including bisazo-, trisazo- and tetrakisazopigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmiumselenide, cadmium sulphide, and mixtures thereof. For some embodiments, the charge generating compound comprises oxytitanium phthalocyanine, hydroxygallium phthalocyanine or a combination thereof.

Generally, a charge generation layer comprises a binder in an amount from about 10 to about 90 weight percent and more preferably in an amount of from about 20 to about 75 weight percent, based on the weight of the charge generation layer. A charge transport layer generally comprises a binder in an amount from about 30 weight percent to about 70 weight percent. A single layer with a charge transport compound and a charge generating compound generally comprises a binder in an amount from about 10 weight percent to about 60 weight percent. A person of ordinary skill in the art will recognize that additional ranges of binder concentrations are contemplated and are within the present disclosure.

The binder generally is capable of dispersing or dissolving the charge transport compound (in the case of the charge transport layer) and the charge generating compound (in the case of the charge generating layer). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymetbacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Preferably, the binder is selected from the group consisting of polycarbonates, polyvinyl butyral, and a combination thereof. Examples of suitable polycarbonate binders include polycarbonate A which is derived from bisphenol-A, polycarbonate Z, which is derived from cyclohexylidene bisphenol, polycarbonate C, which is derived from methylbisphenol A, and polyestercarbonates. Examples of suitable of polyvinyl butyral are BX-1 and BX-5 form Sekisui Chemical Co. Ltd., Japan.

The photoreceptor may optionally have additional layers as well. Such additional layers can be, for example, a sub-layer and overcoat layers such as barrier layers, release layers, and adhesive layers. The release layer forms the uppermost layer of the photoconductor element. The barrier layer may be sandwiched between the release layer and the photoconductive element or used to overcoat the photoconductive element. The barrier layer provides protection from abrasion to the underlayers. The adhesive layer locates and improves the adhesion between the photoconductive element, the barrier layer and the release layer, or any combination thereof. The sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled Barrier Layer For Photoconductor Elements COmprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

Generally, adhesive layers comprise a film forming polymer, such as polyester, polyvinylbutyral, polyvinylpyrolidone, polyurethane, polymethyl methacrylate, poly(hydroxy amino ether) and the like.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be 1–25 microns thick.

The charge transport compounds as described herein, and photoreceptors including these compounds, are suitable for use in an imaging process with either dry or liquid toner development. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, a charge director. In some embodiments of liquid toner, a resin to pigment ratio can be from 2:1 to 10:1, and in other embodiments, from 4:1 to 8:1. Liquid toners are described further in Published U.S. Patent Applications 2002/0128349, entitled "Liquid Inks Comprising A Stable Organosol," 2002/0086916, entitled "Liquid Inks Comprising Treated Colorant Particles," and 2002/0197552, entitled "Phase Change Developer For Liquid Electrophotography," all three of which are incorporated herein by reference.

Charge Transport Compound

In some embodiments, the organophotoreceptors as described herein can comprise an improved charge transport compound with two hydrazone groups conjugated with a carbozole group. Specifically, the compounds are based on a formula:

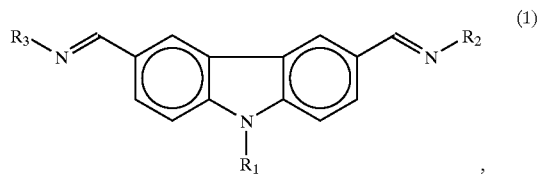

(1)

in which $R_1$ is hydrogen, a branched or linear alkyl group (e.g., a $C_1$–$C_{20}$ alkyl group), a branched or linear unsaturated hydrocarbon group, an ether group, or an aryl group (e.g., a phenyl or naphthyl group), and $R_2$ and $R_3$ each have a nitrogen to form a hydrazone that is bonded to at least one aromatic group. $R_2$ and $R_3$ have independently a structure of:

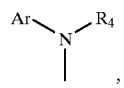

in which Ar is selected form the group consisting of;

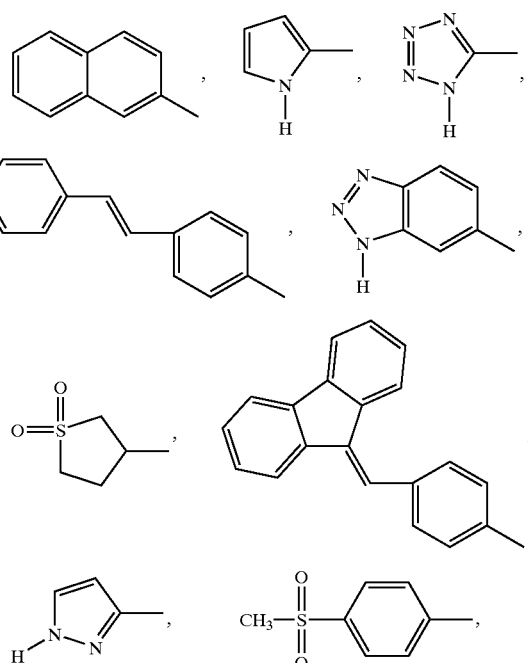

$R_4$ is a hydrogen, or an aromatic group including, for example, a phenyl, napthyl or any of the members of the group specifying Ar.

Non-limiting examples of the charge transport compound of this invention have the following formula:

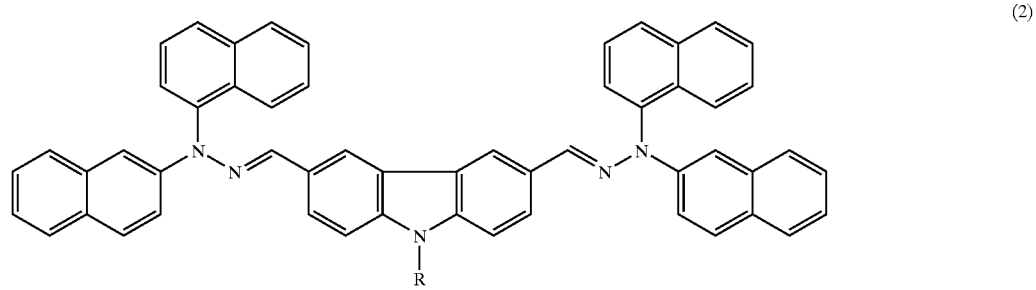

(2)

-continued
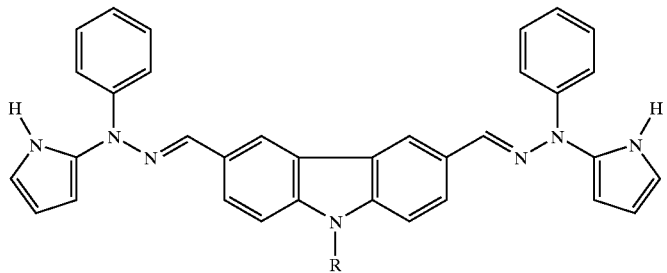
(3)
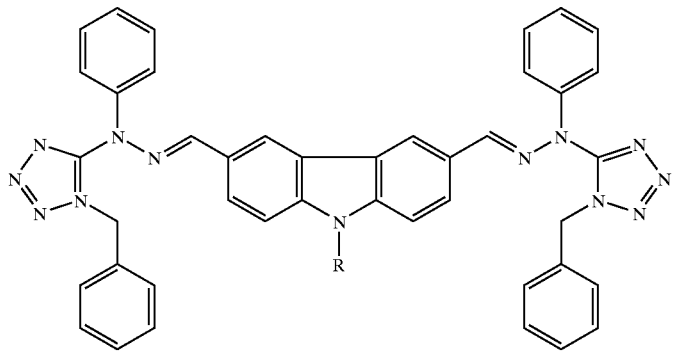
(4)
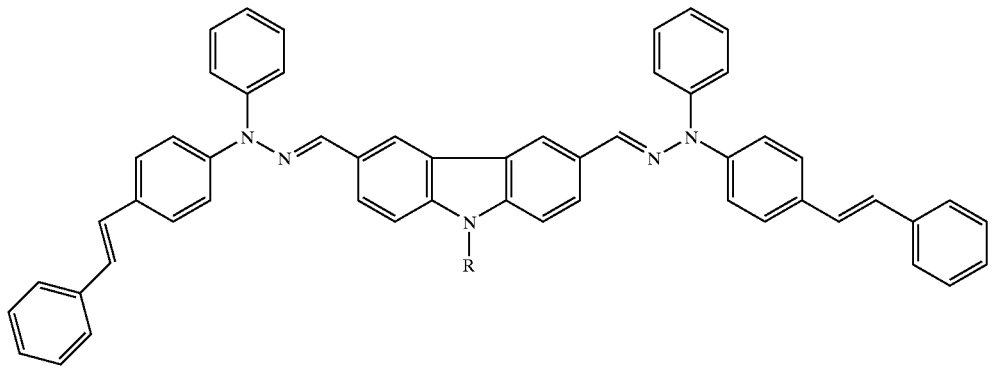
(5)
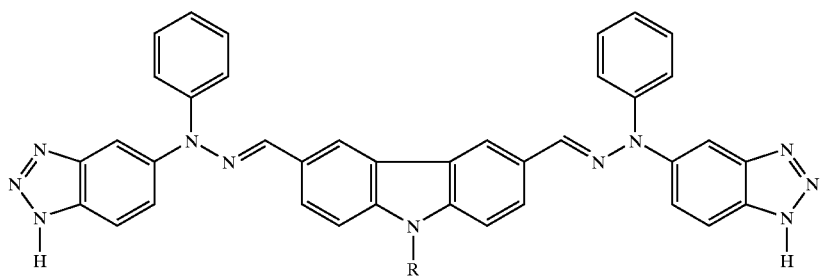
(6)
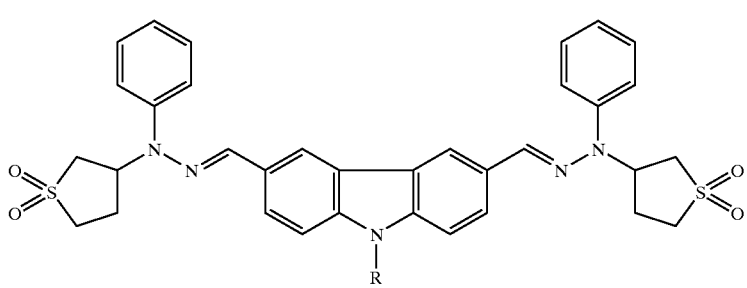
(7)

-continued
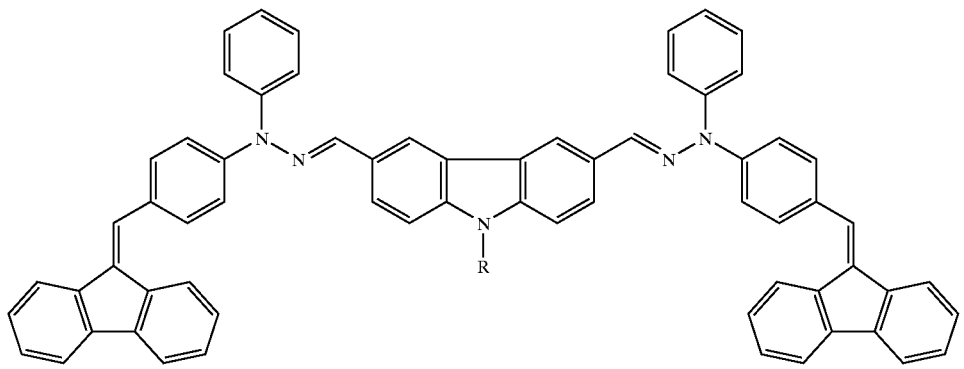
(8)
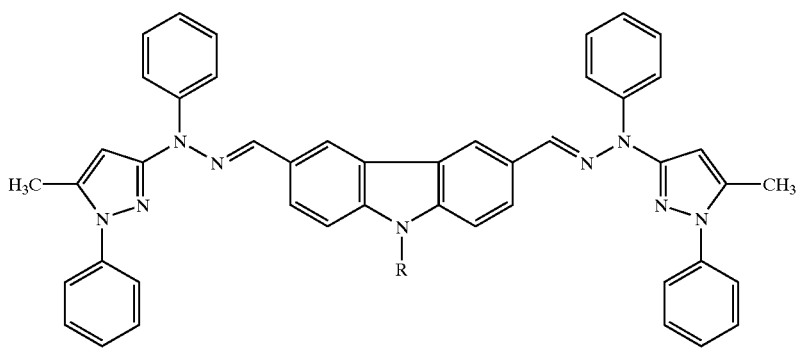
(9)
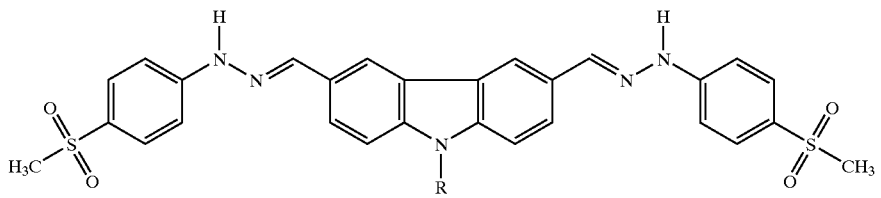
(10)
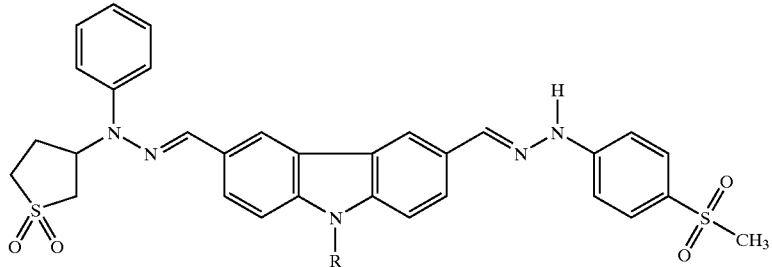
(11)
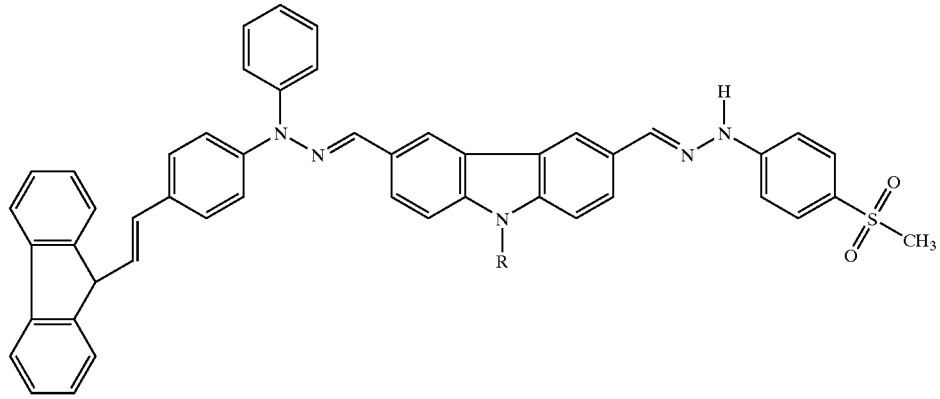
(12)

Synthesis Of Charge Transport Compounds

Charge transport compounds as described herein can be synthesized from a hydrazine and a 3,6-diformylcarbazole in an acid catalyzed reaction. In particular, the reactants are mixed in an approximate ratio of one mole of hydrazine to a half mole of diformylcarbazole along with a catalytic amount of concentrated acid, such as sulfuric acid. The mixture generally can be refluxed for 2 to 16 hours. A crude product is obtained upon evaporation of the solvent. The product can be purified by recrystalization.

For symmetric products, a single hydrazine is used, such that the $R_2$ and $R_3$ groups in formula 1 above is the same. In other embodiments, a mixture of hydrazines can be used to form a mixture of symmetric and non-symmetric products. The non-symmetric products can be formed by reacting the two different hydrazines either simultaneously or sequentially. If the two different hydrazines are reacted simultaneously, the resulting asymmetric and symmetric can be separated from each other, for example, by column chromatography. In other embodiments, a first hydrazine can be reacted with an excess of diformylcarbazole, generally a two to one excess or greater, to form a substituted formylcarbazole. Then, the substituted formylcarbazole is reacted with a second hydrazine to form an asymmetric dihydrazone carbazole.

Synthetic Methods of Hydrazines

The synthesis of some representative hydrzines are described in the following.

1,1-Dinaphthylhydrazine 1,1-Dinaphthylhydrazine can be prepared according to the procedure described in Staschkow, L. I.; Matevosyan, R. O. Journal of the General Chemistry (1964) 34, 136, which is incorporated herein by reference. A suspension of 0.07 mole of the naphthyl nitrosamine in 750 ml of ether is cooled to 5–8° C. and treated with 150 g of zinc dust. Acetic acid (70 ml) is then added drop wise with stirring. To complete the reaction, 40 g of zinc dust is added. The reaction mixture is heated and filtered from the sludge. The mother liquor is washed with 10% sodium carbonate solution and dried with solid KOH. The ether is distilled off to give the crystalline hydrazine, which is crystallized from ethanol or butanol. Other symmetric disubstituted hydrazines can be synthesized based on an equivalent process.

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (53%) having a melting point of 120–121° C. (MeOH).

N-Pyrrol-2-yl-N-phenylhydrazine

N-Pyrrol-2-yl-N-phenylhydrazine can be prepared according to the procedure described in Japanese Patent No. 05148210 by Myamoto, incorporated herein by reference.

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599-608 by Atherton et al., incorporated herein by reference.

N-(4-Stilbenyl)-N-phenylhydrazine

N-(4-Stilbenyl)-N-phenylhydrazine can be prepared according to the procedure described in Zh. Org. Khim. (1967), 3(9), 1605-3 by Matevosyan et al., incorporated herein by reference. Following this procedure, to a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif.; Web: www.spectrumchemical.com) heated to boiling temperature, sodium was slowly added until there was no more discharge of red coloration. After boiling for some time the mixture was dissolved in 1750 ml of ethanol and cooled to −15° C. The precipitated product was recrystallized to give 28% of N-(4-stilbenyl)-N-phenylhydrazine.

N-(5-Benzotriazolyl)-N-phenylhydrazine

N-(5-benzotriazolyl)-N-phenylhydrazine can be prepared according to the procedure that follows. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time the mixture is cooled to room temperature. The product is isolated and purified.

N-Phenyl-N-sulfolan-3-ylhydrazine

N-Phenyl-N-sulfolan-3-ylhydrazine can be prepared according to the procedure described in Great Britain Patent No. 1,047,525 by Mason, incorporated herein by reference. Following this procedure, to a mixture of 0.5 mole of butadiene sulfone (commercially available from Aldrich, Milwaukee, Wis.) and 0.55 mole of phenylhydrazine (commercially available from Aldrich, Milwaukee, Wis.), a 0.005 mole 40% aqueous potassium hydroxide solution was added. The mixture was kept for 2 hours at 60° C. whereupon a solid separated. After 10 hours the solid was filtered off to give N-phenyl-N-sulfolan-3-ylhydrazine (I) (93%) having a melting point of 119–20° C. (MeOH).

N-4-[(9H-fluoren-9-ylidene)benzyl]-N-phenylhydrazine

N-4-[(9H-fluoren-9-ylidene)benzyl]-N-phenylhydrazine can be prepared according to the procedure similar to that described in Zh. Org. Khim. (1967), 3(9), 1605-3 by Matevosyan et al., incorporated herein by reference. Following this procedure, to a mixture of phenylhydrazine (97 g, 0.9 mole, commercially available from Aldrich, Milwaukee, Wis.) and p-9-(4-chlorobenzylidene)fluorene (28.9 g, 0.1 mole, commercially available from from Aldrich, Milwaukee, Wis.) heated to boiling temperature, sodium was slowly added until there was no more discharge of red coloration. After boiling for some time the mixture was dissolved in 1750 ml of ethanol and cooled to −15° C. The precipitated product was recrystallized to give N-4-[(9H-fluoren-9-ylidene)benzyl]-N-phenylhydrazine.

5-Methyl-1-Phenyl-3-(1-Phenylhydrazino)-Pyrazole

5-Methyl-1-phenyl-3-(1-phenylhydrazino)-pyrazole can be prepared according to the procedure described in J. Chem. Soc. C (1971), (12), 2314–17 by Boyd et al., incorporated herein by reference.

4-Methylsulfonylphenylhydrazine (Registry Number 877-66-7)

4-Methylsulfonylphenylhydrazine is commercially available from Fisher Scientific USA, Pittsburgh, Pa. (1-800-766-7000).

Synthetic Methods for Diformylcarbazoles

In general, diformylcarbozoles can be synthesized from commercially available carbozole. In some embodiments, the carbazole can be first substituted at the nitrogen. In general, the nitrogen can be substituted by reacting the carbazole with a halogenated organic group, especially a brominated group, such as a brominated alkyl group. The reaction generally is alkaline catalyzed. Specific reactions for the synthesis of specific N-substituted carbozoles are described in the Examples below. After isolated the nitrogen-substituted carbozole, if relevant, the carbozole or nitrogen-substituted carbozole can be reacted to form diformyl substituted carbozole using N,N-dimethylformamide (DMF).

As a specific example, in one embodiment, a 271 ml quantity of DMF (3.5 mol) can be added to a 1-liter, 3-neck round bottom flask equipped with mechanical stirrer, thermometer, and addition funnel. The contents can be cooled in a salt/ice bath. When the temperature inside the flask reached 0° C., 326 ml of $POCl_3$ (3.5 mol) can be slowly added. During the addition of $POCl_3$, the temperature inside the flask is not allowed to rise above 5° C. After the addition of $POCl_3$ is completed, the reaction mixture can be allowed to warm to room temperature. A 126 g quantity of N-heptylcarbazole can be then added, and the flask can be heated to 90° C. for 24 hr. using a heating mantle. The reaction mixture can be cooled to room temperature, and the solution can be added slowly to a 4.5 liter beaker containing a solution of 820 g sodium acetate dissolved in 2 liters of water. The beaker can be cooled in an ice bath and stirred for 3 hr. The brownish solid obtained can be filtered and washed repeatedly with water, followed by a small amount of ethanol (50 ml). For a N-heptyl carbazole starting material, the resulting product was recrystallized once from toluene using activated charcoal and dried under vacuum in an oven heated at 70° C. for 6 hr to obtain 80 g (51% yield) of N-heptyl-3,6-diformyl-carbazole.

Organophotoreceptor (OPR) Preparation Methods

Following conventional terminology, the number of layers in the OPR refers to the layers with charge transport compounds and/or charge generating compounds. Thus, the presence of overlayers, underlayers, release layers and the like do not alter the single layer versus dual layer terminology.

Positive Inverted Dual Layer OPR

A positive polarity, inverted dual layer organic photoreceptor can be prepared by incorporating a charge transport compound disclosed herein into the charge transport layer and then over coating this layer with a charge generation solution to form a charge generation layer. The positive inverted dual layer is designed to operate with a positive surface charge that is discharge upon illumination at the point of illumination. An example of a specific approach for forming this structure is presented below.

In one embodiment, a charge transport solution comprising a 1:1 ratio by weight of a charge transport compound as described herein to a binder, such as polycarbonate Z binder (commercially available from Mitsubishi Gas Chemical under the trade name Lupilon™ Z-200 resin), can be prepared by combining a solution of 1.25 g of one of the charge transport compounds as described herein in 8.0 g of tetrahydrofuran with 1.25 g of polycarbonate Z in 6.25 g of tetrahydrofuran. The charge transport solution can be hand-coated onto a 76-micrometer (3-mil) thick aluminized polyester substrate (such as a Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 51-micrometer (2-mil) orifice between the blade and polyester, can be used to prepare a film with an 8–10-micron thickness after drying the wet film in an oven at 110° C. for 5–10 min.

A dispersion for forming a charge generation layer can be prepared by micronising 76.1 g of oxytitanium phthalocyanine pigment (H. W. Sands Corp., Jupiter, Fla.), 32.6 g of S-Lec B Bx-5 polyvinylbutryal resin (Sekisui Chemical Co. Ltd.), and 641.3 g of methyl ethyl ketone, using a horizontal sand mill operating in recycle mode for 8 hours. After milling, the charge generation layer base can be diluted with methyl ethyl ketone to decrease the total solids of the solution to 4.0 wt %. The charge generation solution can be hand-coated onto the charge transport layer using a knife coater, set to a 20–25 micron (0.8–1.0 mil) orifice between the blade and charge transport layer to prepare a sub-micron thick charge generation layer (CGL) film after drying the wet film in an oven at 110° C. for 3–5 min.

Negative Dual Layer OPR

A negative polarity, dual layer organic photoreceptor can be prepared forming a charge generation layer and then incorporating a charge transport compound disclosed herein into a solution and coating this solution over the charge generation layer to form a charge transport layer. A negative dual layer is designed to operate with a negative surface charge that is discharged upon illumination at the point of illumination. A specific example for forming a negative dual layer is described below.

In one embodiment, a charge generation layer mill-base dispersion can be prepared by micronising 76.1 g of oxytitanium phthalocyanine pigment, 32.6 g of S-Lec B Bx-5 polyvinylbutryal resin (Sekisui Chemical Co. Ltd.), and 641.3 g of methyl ethyl ketone, using a horizontal sand mill operating in recycle mode for 8 hours. Following milling the charge generating layer base can be diluted with methyl ethyl ketone to decrease the total solids of the solution to 4.0 wt %. The charge generation solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 20–25 micron (0.8–1.0 mil) orifice between the blade and substrate, can be used to prepare the sub-micron thick charge generating layer film after drying the wet film in an oven at 110° C. for 3–5 min.

A charge transport solution comprising a 1:1 ratio by weight of a charge transport compound described herein to polycarbonate Z binder is prepared by combining a solution of 1.25 g of the charge transport compound in 8.0 g of tetrahydrofuran with 1.25 g of polycarbonate Z in 6.25 g of tetrahydrofuran. A knife coater, set to a 51-micrometer (2-mil) orifice between the blade and polyester, can be used to prepare an 8–10-micron thick film after drying the wet film in an oven at 110° C. for 5–10 min.

Single Layer OPR

A single layer organic photoreceptor can be prepared by incorporating a charge transport compound disclosed herein along with a charge generating composition into a single coating solution and then coating this solution over a suitable substrate. A single layer OPR, in principle, can be designed to operate with a surface charge, which may be positive or negative, that is discharged upon illumination at the point of illumination in which the charge is generated in a layer and transported through that layer.

In practice, single layer OPRs are used predominantly with positive surface charges. In general, through the photoconductive and semiconductive materials of interest, electrons have a significantly lower mobility that holes. With low concentrations of charge generating pigment compounds to limit charge trapping in a single layer structure, the electron-hole pairs can be generated some distance from the surface of the OPR after light is absorbed. However, the electron-hole pairs still tend to be closer to the surface than the substrate, such that the electron has less distance to travel than the hole in a positive single layer OPR. The hole from the electron-hole pair can transport through the remaining portion of the OPR to the underlying substrate. Thus, while electrons may travel some distance to neutralize positive charges at the surface of a positively charged OPR, the electrons would still have significantly larger distance to travel to the substrate in a negative single layer OPR. For single layer embodiments, it can be desirable to include an optional electron transport compound to facilitate the electron transport.

However, the use of a dual layer positive OPR is complicated by the formation of a thin charge generating layer over a charge transport layer due to processing complications of dip coating and solvent selection. Also, the thin charge generating layer can be abraded away in use without a good overcoat layer. Thus, a single layer positive OPR may offer some advantages over a positive dual layer system. Since the formation of negative dual layer OPRs do not have the complications of positive dual layer OPRs and since limited electron mobility hinders operation of negative single layer OPRs, negative single layer OPRs generally are less desirable although they are within the scope of the present disclosure for incorporation of the improved charge transport compounds described herein.

In one embodiment especially for the preparation of a single layer OPR, a charge transport pre-mix solution containing a 1:1 ratio by weight of a charge transport compound disclosed herein to polycarbonate Z binder can be prepared by combining a solution of 1.25 g of the charge transport compound in 8.0 g of tetrahydrofuran with 1.25 g of polycarbonate Z in 6.25 g of tetrahydrofuran. A charge generating layer mill-base dispersion can be prepared by micronising 76.1 g of oxytitanium phthalocyanine pigment, 32.6 g of polycarbonate Z binder resin, and 641.3 g of tetrahydrofuran, using a horizontal sand mill operating in pass mode for 6–8 passes. An electron transport pre-mix solution containing a 1:1.4 ratio of (4-n-butoxycarbonyl-9-fluorenylidene) malonitrile electron transport compound to Polycarbonate Z binder can be prepared by combining a solution of 1.25 g of one of the electron transporting material in 8.0 g of tetrahydrofuran with 1.75 g of polycarbonate Z in 9 g of tetrahydrofuran.

The single layer coating solution can be prepared by combining 14 g of the charge transport pre-mix, 4.08 g of the electron transport premix and 1.92 g of the charge generating layer mill-base dispersion. The single layer solution can be hand-coated onto a 76-micrometer (3-mil) thick aluminized polyester substrate (Melinex® 442 polyester film from Dupont having a 1 ohm/square aluminum vapor coat) having a 0.3-micron polyester resin sub-layer (Vitel® PE-2200 from Bostik Findley, Middletown, Mass.). A knife coater, set to a 50–75 micron (2–3 mil) orifice between the blade and substrate, can be used to prepare a single layer film with an 8–10 micron thickness after drying the wet film in an oven at 110° C. for 5–10 min.

The invention will now be described further by way of the following examples.

EXAMPLES

Example 1
Synthesis Of Specific Carbazoles

For the synthesis of N-Heptyl-3,6-Diformylcarbazole, to a 1 liter 3-neck round bottom flask equipped with reflux condenser and mechanical stirrer were added 88.69 g carbazole (0.53 mol, commercially available from Aldrich, Milwaukee, Wis.), 100 g 1-bromoheptane (0.56 mol, commercially available from Aldrich, Milwaukee, Wis.), 6.00 g benzyltriethyl ammonium chloride (0.026 mol, commercially available from Aldrich, Milwaukee, Wis.) and 400 ml of toluene. The mixture was stirred at room temperature for 0.5 hr., followed by the addition of an aqueous solution of NaOH (prepared by dissolving 100 g of NaOH in 100 g water). The mixture was refluxed for 5 hr. and cooled to room temperature. The organic phase was separated and washed repeatedly with water until the pH of the washing water was neutral. The organic phase was dried over $Mg_2SO_4$, filtered, and evaporated to dryness to obtain 126 g of brown liquid (89% yield).

For the preparation of N-Dodecyl-3,6-Diformylcarbazole, N-dodecyl carbazole was prepared from carbazole (66 g, 0.40 mol), 1-bromododecane (100 g, 0.41 mol, commercially available from Aldrich, Milwaukee, Wis.), benzyltriethyl ammonium chloride (4.48 g, 0.02 mol), toluene (400 ml), and sodium hydroxide (200 g of 50% aqueous solution) according to the procedure described for N-Heptylcarbazole.

N-dodecyl-3, 6-diformyl carbazole was prepared from DMF (186 ml, 2.4 mol), $POCl_3$ (224 ml, 2.4 mol), and N-dodecylcarbazole (115 g, 0.34 mol), according to the procedure described for N-Hepyl-3,6-Diformylcarbazole. The product was recrystallized once from THF/water to yield 100 g of a brown solid (75% yield).

For the synthesis of N-Tridecyl-3,6-Diformylcarbazole, N-tridecylcarbazole was prepared from carbazole (62.43 g, 0.37 mol), 1-bromotridecane (100 g, 0.38 mol, commercially available from Aldrich, Milwaukee, Wis.), benzyltriethyl ammonium chloride (4.24 g. 0.018 mol), toluene (400 ml), and 50% aqueous NaOH (200 g) according to the procedure described for N-heptylcarbazole. The product was obtained as 120 g of brown liquid (96% yield).

N-tridecyl-3, 6-diformyl carbazole was prepared from DMF (186 ml, 2.4 mol), $POCl_3$ (224 ml, 2.4 mol), and N-tridecylcarbazole (120 g, 0.34 mol) according to the procedure described for N-heptyl-3,6-Diformylcarbazole. The product was recrystallized from THF/water to yield 130 g (84% yield) of purified product.

For the preparation of N-Tetradecyl-3,6-Diformylcarbazole, N-tetradecylcarbazole was prepared from carbazole (59.27 g, 0.35 mol), 1-bromotetradecane (100 g, 0.36 mol, commercially available from Aldrich, Milwaukee, Wis.), benzyltriethyl ammonium chloride (4.00 g, 0.018 mol), 50% aqueous NaOH (200 g), and toluene (400 ml) according to the procedure described for N-Heptylcarbazole. The product was obtained as 120 g of a brown liquid (93% yield). Upon standing at room temperature overnight, the liquid solidified N-tetradecyl-3,6-diformylcarbazole was prepared from DMF (186 ml, 2.4 mol), $POCl_3$ (224 ml, 2.4 mol), and N-tetradecylcarbazole (120 g, 0.33 mol) according to the procedure described for N-Heptyl-3,6-Diformylcarbazole. 117 g of product were obtained (84% yield).

For the synthesis of N-propylphenyl-3,6-Diformylcarbazole, N-propylphenylcarbazole was prepared from carbazole (82.18 g, 0.49 ml), 1-bromo-3-phenylpropane (100 g, 0.50 mol, commercially available from Aldrich, Milwaukee, Wis.), benzyltriethyl ammonium chloride (5.58 g, 0.025 mol), toluene (400 ml), and 50% aqueous NaOH (200 g) according to the procedure described for N-Heptylcarbazole. 108 g of the product was obtained as a white solid (77% yield).

N-propylphenyl-3, 6-diformyl carbazole was prepared from DMF (204 ml, 2.64 mol), $POCl_3$ (246 ml, 264 mol), and N-propylphenylcarbazole (107.84 g, 0.38 mol) according to the procedure described for Compound N-Heptyl-3, 6-Diformylcarbazole. A brownish solid was obtained which was recrystallized from THF/water to yield 91.5 g (70% yield) of the product.

For the synthesis of N-2-Ethylhexyl-3,6-Diformylcarbazole, N-2-ethylhexylcarbazole was prepared from carbazole (85.09 g, 0.51 mol), 2-ethylhexylbromide (100 g, 0.52 mol, commercially available from Aldrich, Milwaukee, Wis.), benzyltriethyl ammonium chloride (5.78 g, 0.025 mol), toluene (400 ml), and 50% aqueous NaOH solution (200 g) according to the procedure described for N-heptylcarbazole. The product was obtained as 115 g of brownish liquid (81% yield).

N-2-ethylhexyl-3,6-diformyl carbazole was prepared from DMF (97 ml, 1.25 mol), $POCl_3$ (116.5 ml, 1.25 mol), and N-2-ethylhexylcarbazole (50 g, 0.18 mol) according to the procedure described for N-Heptyl-3,6-Diformylcarbazole. The product was obtained as 40 g of brownish liquid (66% yield). The product was used as is in the next step without any purification.

For the synthesis of N-Pentyl-3,6-Diformylcarbazole, N-Pentylcarbazole was prepared from carbazole (66 g, 0.40 mol), 1-bromopentane (62 g, 0.41 mol, commercially available from Aldrich, Milwaukee, Wis.), benzyltriethyl ammonium chloride (4.48 g, 0.02 mol), toluene (400 ml), and sodium hydroxide (200 g of 50% aqueous solution) according to the procedure described for N-Heptylcarbazole N-Pentyl-3, 6-diformyl carbazole was prepared from DMF (186 ml, 2.4 mol), $POCl_3$ (224 ml, 2.4 mol), and N-Pentylcarbazole (81 g, 0.34 mol), according to the procedure described for N-Hepyl-3,6-Diformylcarbazole.

For the synthesis of N-Decyl-3,6-Diformylcarbazole, N-Decyl carbazole was prepared from carbazole (66 g, 0.40 mol), 1-bromodecane (91 g, 0.41 mol, commercially available from Aldrich, Milwaukee, Wis.), benzyltriethyl ammonium chloride (4.48 g, 0.02 mol), toluene (400 ml), and sodium hydroxide (200 g of 50% aqueous solution) according to the procedure described for N-Heptylcarbazole N-dodecyl-3, 6-diformyl carbazole was prepared from DMF (186 ml, 2.4 mol), $POCl_3$ (224 ml, 2.4 mol), and N-decylcarbazole (104 g, 0.34 mol), according to the procedure described for N-Hepyl-3,6-Diformylcarbazole.

Example 2
Synthesis And Characterization of Hydrazones

This example presents specific procedures for the synthesis of specific hydrazone compounds described above. These compounds are characterized by spectroscopic techniques. The number refers to the formula numbers above.
Compound 7

N-Phenyl-N-sulfolan-3-ylhydrazine (2.16 g, 0.01 mol, prepared previously) and 40 ml of THF/MeOH (1:1) were added to a 100 ml round bottom flask equipped with reflux condenser and magnetic stirrer. The solution was stirred at room temperature for 5 minutes until all solid entered into solution. Then, $K_2CO_3$ (1.52 g, 0.011 mol, obtained from Aldrich) was added into the reaction mixture. The mixture was stirred for 15 minutes at room temperature followed by the addition of N-ethyl-3, 6-diformylcarbazole (1.29 g, 0.005 mol, prepared in similar method to the other N-alkyl-3,6-diformyl derivatives mentioned previously) in two portions. The reaction mixture was refluxed for 24 hours then cooled to room temperature and the solid was filtered off. The product was crystallized from a mixture of methanol/THF (1:1) and dried at 50° C. vacuum oven for 5 hours to obtain 1.51 g of product (Yield=49.03%).

The product had a melting point of 214.5–215° C. The product was soluble in DMSO, toluene, THF, DMF, benzene and acetone. The product had a proton NMR spectrum with peaks interpreted as follows: $^1$H NMR (Benzene): δ=0.80 (t, 3H, C$\underline{H_3}$—CH$_2$—), 1.83 (q, 2H, CH$_3$—C$\underline{H_2}$—), 2.75–2.20 (m, 4H, —CH—C$\underline{H_2}$—CH$_2$—), 3.22–2.78 (m, 4H, —C$\underline{H_2}$—CH$_2$—S—), 3.71–3.40 (m, 4H, —CH—C$\underline{H_2}$—S—), 3.82 (p, 2H, —CH—C$\underline{H}$—CH$_2$—), 7.54 (s, 2H, Ar—C$\underline{H}$=N—), 8.13–7.62 and 7.09–6.75 (m, 16H aromatic protons). The infrared spectrum of the product had peaks that were interpreted as follows: IR (KBr): 3050 (Aromatic), 2950 (Aliphatic), 2880 (Aliphatic), 1600 (—C=N—), 1320 (—SO$_2$—).

Compound 10

Methylsulfonylphenylhydrazine hydrochloride (1.08 g, 0.007 mol, available from Fisher Scientific USA, Pittsburgh, Pa., Phone # 1-800-766-7000) and 40 ml of THF/MeOH (1:3) containing 5 ml of triethylamine were added to a 100 ml round bottom flask equipped with magnetic stirrer and reflux condenser. The mixture was stirred at room temperature until all solid entered into solution followed by the addition of N-ethyl-3,6-diformylcarbazole (0.91 g, 0.003 mol, prepared in similar method to the other N-alkyl-3,6-diformyl derivatives mentioned previously) in two portions. The reaction mixture was refluxed for 24 hours. The product was purified by column chromatography (hexane/ethylacetate: 1/2) to obtain 0.49 g product (Yield=31.18%).

The product had a melting point of 196° C. The product was soluble in DMSO, toluene, THF, DMF, and chloroform. The product had a proton NMR spectrum with peaks interpreted as follows: $^1$H NMR (DMSO): δ=1.35 (t, 3H, C$\underline{H_3}$—CH$_2$—), 3.12 (s, 6H, C$\underline{H_3}$—S), 4.55 (q, 2H, CH$_3$—C$\underline{H_2}$—), 7.19–8.63 (m, 14H, aromatic protons and 2H,Ar-C$\underline{H}$=N—), 10.83 (s, 2H, NH). The infrared spectrum of the product had peaks that were interpreted as follows: IR (KBr): 3280 (NH), 3030 (Aromatic), 2950 (Aliphatic), 2930 (Aliphatic), 1600 (—C=N—), 1320 (—SO$_2$—).

Example 3
Ionization Potential

This example provides measurements of the ionization potential for the two charge transport compounds synthesized as described in Example 2.

Samples for ionization potential (Ip) measurements were prepared by dissolving the compound in tetrahydrofuran. The solution was hand-coated on an aluminized polyester substrate that was precision coated with a methylcellulose-based adhesion sub-layer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of both the sub-layer and CTM layer was ~0.4 μm. No binder material was used with CTM in the preparation of the samples for Ip measurements.

The ionization potential was measured by the electron photoemission in air method similar to that described in "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama, which is hereby incorporated by reference. The samples were illuminated with monochromatic light from a quartz monochromator with a deuterium lamp source. The power of the incident light beam was 2–5·10⁻⁸ W. The negative voltage of −300 V was supplied to the sample substrate. The counter-electrode with the 4.5×15 mm² slit for illumination was placed at 8 mm distance from the sample surface. The counter-electrode was connected to the input of the BK2-16 type electrometer, working in the open impute regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}$=f(hv) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis", *Electrophotography*, 28, Nr. 4, p. 364. (1989) by E. Miyamoto, Y. Yamaguchi, and M. Yokoyama; and "Photoemission in Solids", Topics in Applied Physics, 26, 1–103. (1978) by M. Cordona and L. Ley, incorporated herein by reference]. The linear part of this dependence was extrapolated to the hv axis and Ip value was determined as the photon energy at the interception point. The ionization potential measurement has an error of ±0.03 eV.

The ionization potential data for compounds 7 and 10 are listed in Table 1.

TABLE 1

| Compound | $\mu_0$ (cm²/V · s) | $\mu$(cm²/V · s) at 6.4 · 10⁵ V/cm | $\alpha$ (cm/V)$^{0.5}$ | Ionization Potential (eV) |
|---|---|---|---|---|
| Compound 7 | 10⁻⁹ | 8.10⁻⁸ | 0.0054 | 5.65 |
| Compound 10 | n/a | n/a | n/a | 5.60 |

Example 4

Hole Mobility

This example presents hole mobility measurements for some of the charge transport compounds synthesized as described in Example 1.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pazera, which is hereby incorporated by reference. Positive corona charging created electric field inside the CTM layer. The charge carriers were generated at the layer surface by illumination with pulses of nitrogen laser (pulse duration was 2 ns, wavelength 337 nm). The layer surface potential decreased as a result of pulse illumination up to 1–5% of initial pre-illumination potential. The capacitance probe that was connected to the wide frequency band electrometer measured the speed of the surface potential dU/dt. The transit time tt was determined by the change (kink) in the curve of the dU/dt transient in linear or double logarithmic scale. The drift mobility was calculated by the formula $\mu$=d²/U₀·t$_t$, where d is the layer thickness and U₀ is the surface potential at the moment of illumination.

To prepare sample for the measurements, a mixture of 0.1 g of the charge transport compound and 0.1 g of polycarbonate Z 200 (S-LEC B BX-1, commercially obtained from Sekisui) was dissolved in 2 ml of THF. The solution was coated on the polyester film with conductive Al layer by the dip roller method. After drying for 1 h at 80° C., a clear 10 μm thick layer was formed. A sample was prepared for compound 7. The hole mobility of the sample was measured and the results are presented in Table 1. Mobility values at electric field strength, E, of 6.4·10⁵ V/cm are given in the Table 1 along with zero field mobilities $\mu_0$. The mobility field dependencies may be approximated by the function:

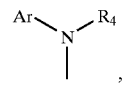

where α is parameter characterizing mobility field dependence. The value of the parameter α is also given in Table 1.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising:

(a) a charge transport compound having the formula:

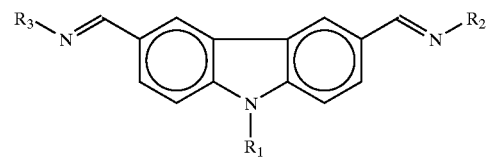

where R₁ is hydrogen, a branched or linear alkyl group, a branched or linear unsaturated hydrocarbon group, an ether group, or an aryl group; and R₂ and R₃ independently have a structure of:

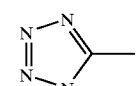

in which Ar is selected from the group consisting of:

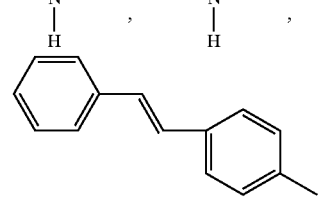

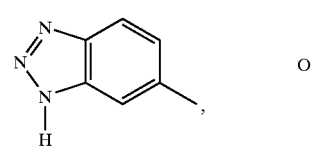 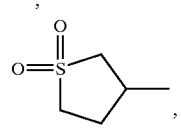

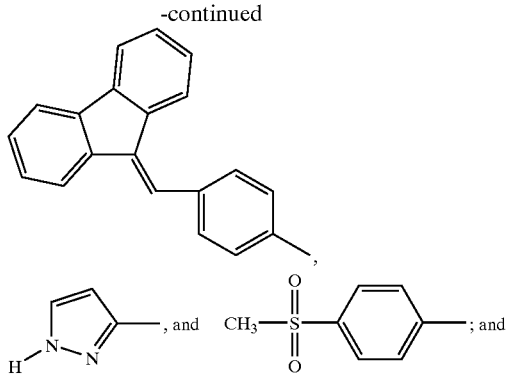

$R_4$ is a hydrogen, or an aromatic group;

(ii) a charge generating compound; and
(iii) an electrically conductive substrate over which said charge transport compound and said charge generating compound are located.

2. An organophotoreceptor according to claim 1 wherein said organophotoreceptor is in the form of a flexible belt.

3. An organophotoreceptor according to claim 1 wherein said organophotoreceptor is in the form of a drum.

4. An organophotoreceptor according to claim 1 comprising:
(a) a charge transport layer comprising said charge transport compound and a polymeric binder; and
(b) a charge generating layer comprising said charge generating compound and a polymeric binder.

5. An organophotoreceptor according to claim 1 wherein said charge transport compound is selected from the group consisting of the following chemical groups:

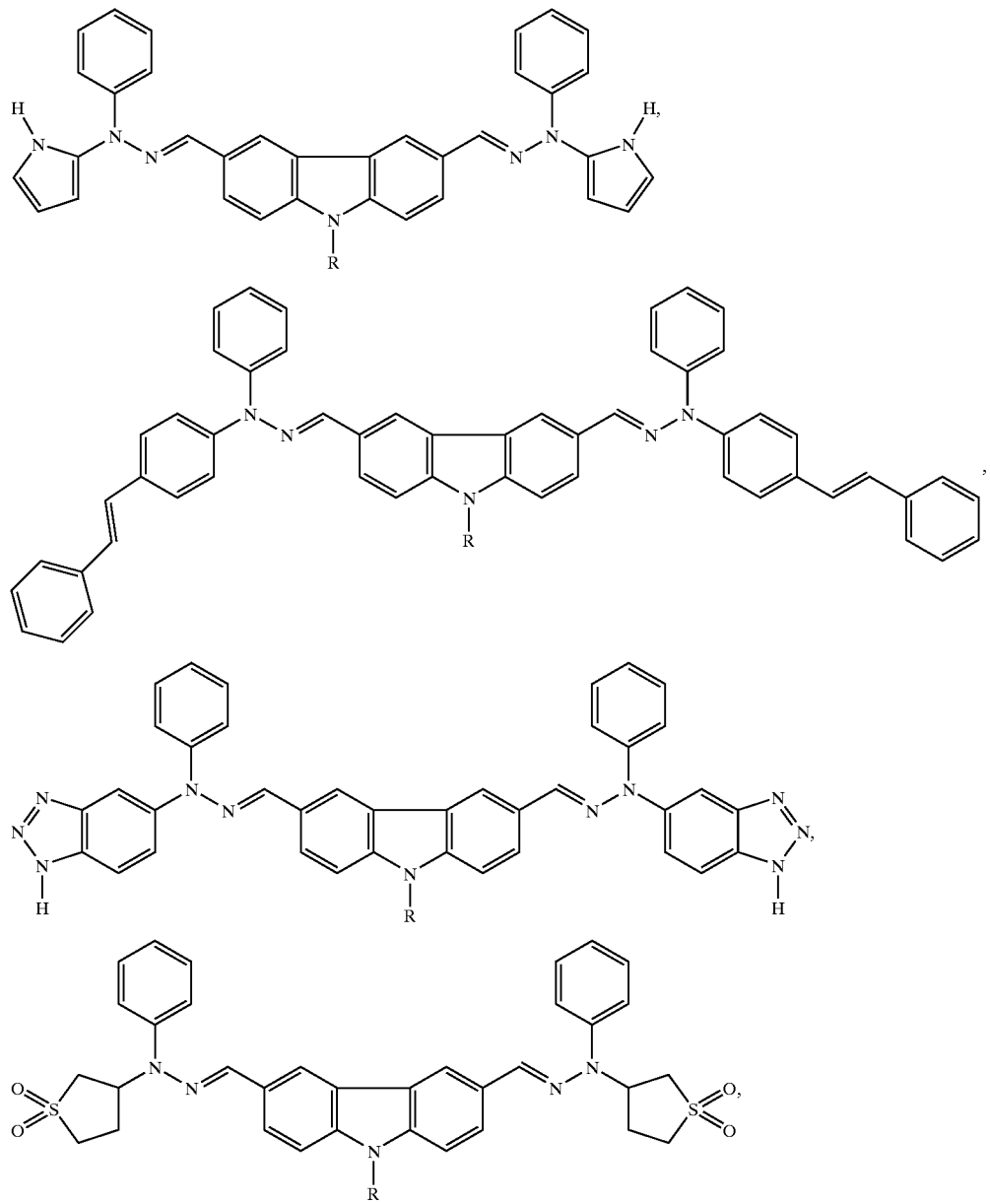

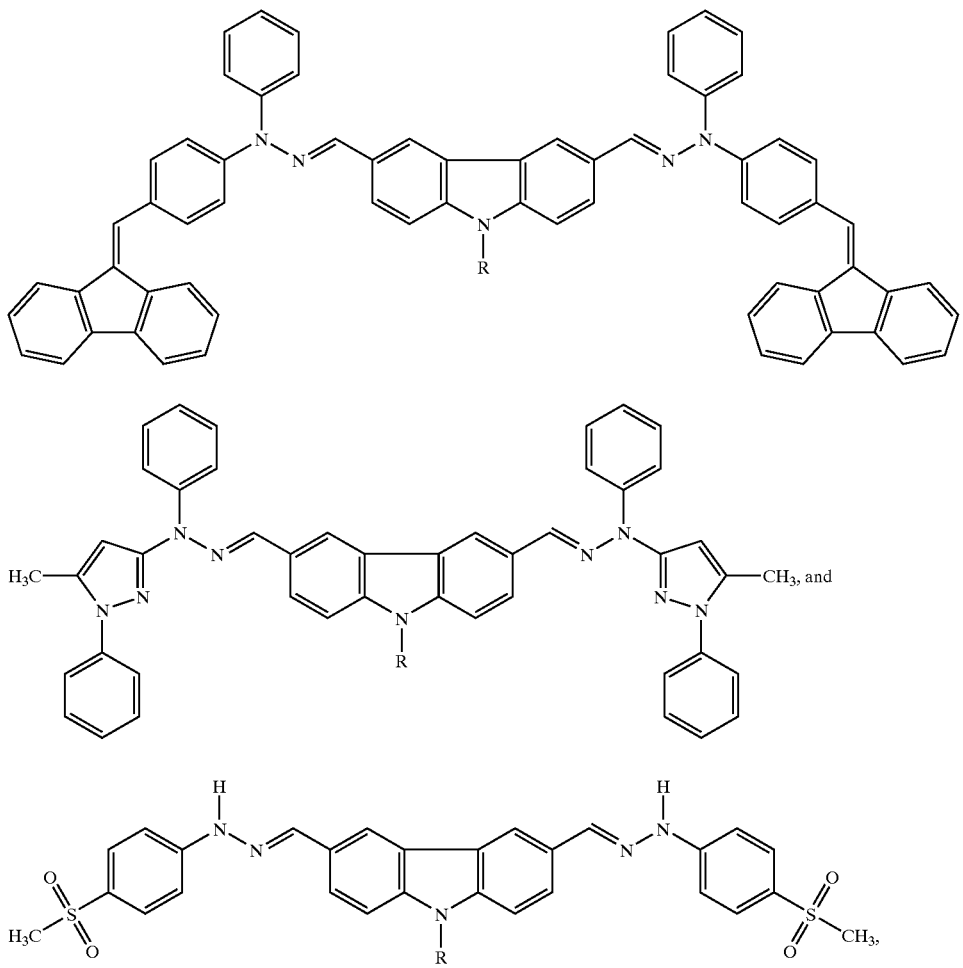

where R is hydrogen, a branched or linear alkyl group, a branched or linear unsaturated hydrocarbon group, an ether group, or an aryl group.

6. An organophotoreceptor according to claim 1 wherein said charge transport compound comprises:

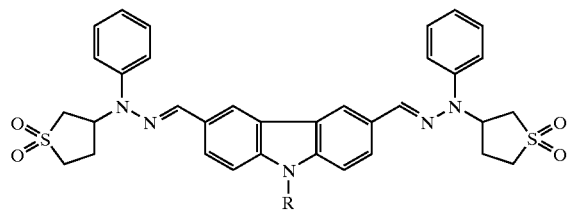

where R is hydrogen, a branched or linear alkyl group, a branched or linear unsaturated hydrocarbon group, an ether group, or an aryl group.

7. An organophotoreceptor according to claim 1 wherein said charge transport compound comprises:

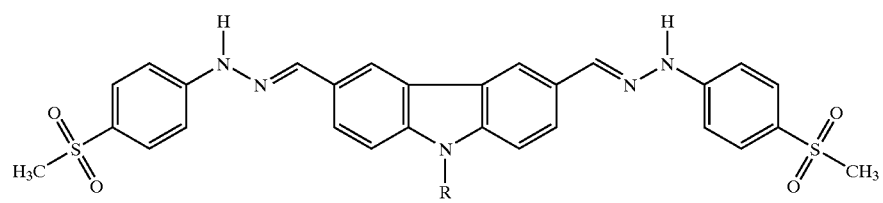

where R is hydrogen, a branched or linear alkyl group, a branched or linear unsaturated hydrocarbon group, an ether group, or an aryl group.

8. An organophotoreceptor comprising:

(a) a charge transport compound having the formula:

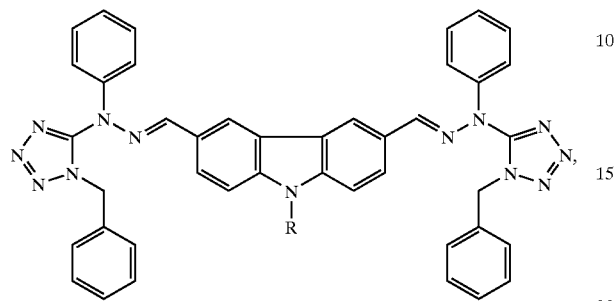

where R is hydrogen, a branched or linear alkyl group, a branched or linear unsaturated hydrocarbon group, an ether group, or an aryl group;

(ii) a charge generating compound; and (iii) an electrically conductive substrate over which said charge transport compound and said charge generating compound are located.

9. An electrophotographic imaging apparatus comprising:

(a) a plurality of support rollers; and (b) an organophotoreceptor operably coupled to said support rollers with motion of said support rollers resulting in motion of said organophotorecepter, said organophotoreceptor comprising:

(i) a charge transport compound having the formula:

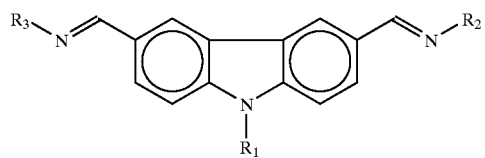

where $R_1$ is hydrogen, a branched or linear alkyl group, a branched or linear unsaturated hydrocarbon group, an ether group, or an aryl group and $R_2$ and $R_3$ independently have a structure of:

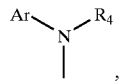

in which Ar is selected from the group consisting of:

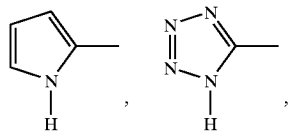

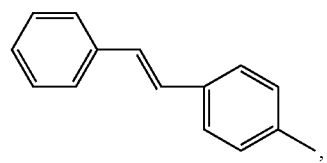

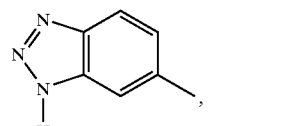, 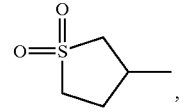

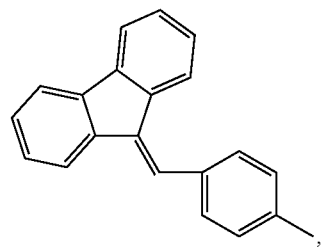

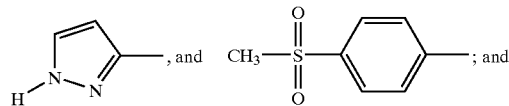 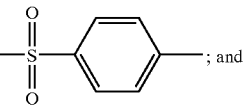

$R_4$ is a hydrogen or an aromatic group;

(ii) a charge generating compound, and (iii) an electrically conductive substrate over which said charge transport compound and said charge generating compound are located.

10. The electrophotographic imaging apparatus according to claim 9 comprising a liquid toner dispenser.

11. An electrophotographic imaging apparatus according to claim 9 wherein said charge transport compound comprises:

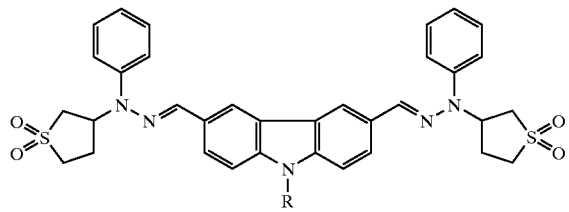

where R is hydrogen, a branched or linear alkyl group, a branched or linear unsaturated hydrocarbon group, an ether group, or an aryl group.

12. An electrophotographic imaging apparatus according to claim 9 wherein said charge transport compound comprises:

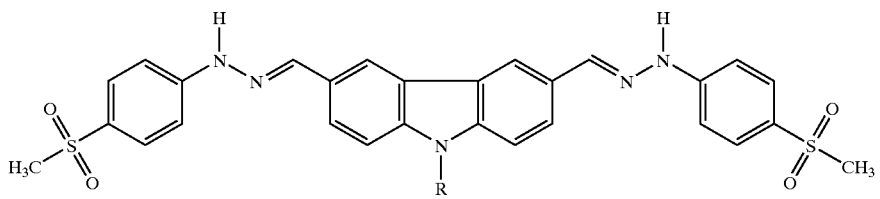

where R is hydrogen, a branched or linear alkyl group, a branched or linear unsaturated hydrocarbon group, an ether group, or an aryl group.

13. An electrophotographic imaging process comprising:

(a) applying an electrical charge to a surface of an organophotoreceptor comprising:
(i) a charge transport compound having the formula:

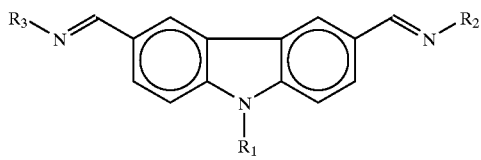

where $R_1$ is hydrogen, a branched or linear alkyl group, a branched or linear unsaturated hydrocarbon group, an ether group, or an aryl group; and
$R_2$ and $R_3$ independently have a structure of:

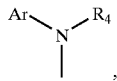

in which Ar is selected from the group consisting of:

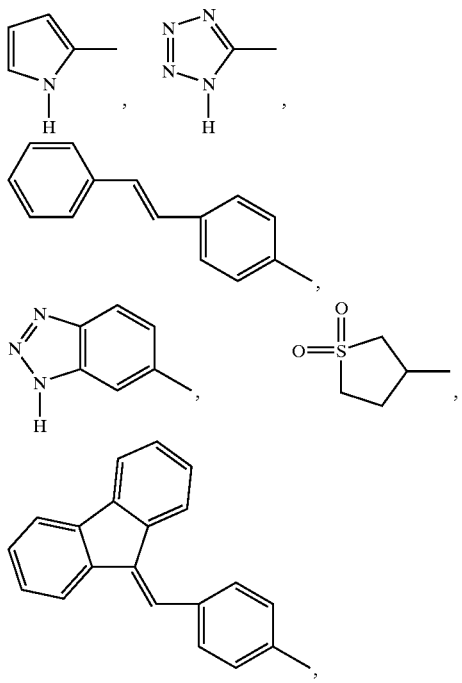

-continued

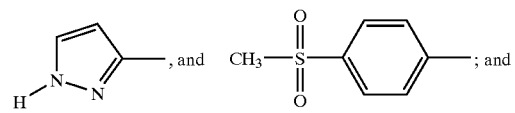

$R_4$ is a hydrogen or an aromatic group;
(ii) a charge generating compound; and
(iii) an electrically conductive substrate;

(b) imagewise exposing said surface of said organophotoreceptor to radiation to dissipate charge in selected areas and thereby form a pattern of charged and uncharged areas on said surface;

(c) contacting said surface with a toner to create a toned image; and (d) transferring said toned image to a substrate.

14. The electrophotographic imaging process according to claim 13 wherein said toner comprises a liquid toner that comprises a dispersion of colorant particles in an organic liquid.

15. An electrophotographic imaging process according to claim 13 wherein said charge transport compound comprises:

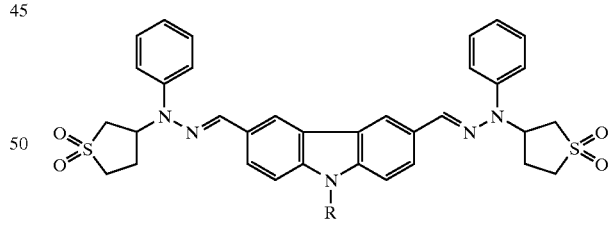

where R is hydrogen, a branched or linear alkyl group, a branched or linear unsaturated hydrocarbon group, an ether group, or an aryl group.

16. An electrophotographic imaging process according to claim 13 wherein said charge transport compound comprises:

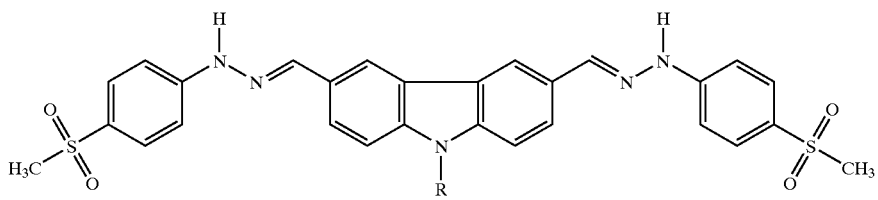

where R in hydrogen, a branched or linear alkyl group, a branched or linear unsaturated hydrocarbon group, an ether group, or an aryl group.

17. A charge transport compound having the formula:

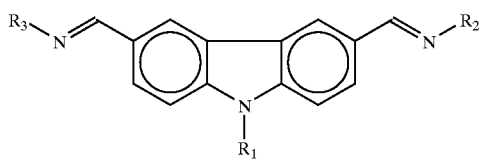

where $R_1$ is hydrogen, a branched or linear alkyl group, a branched or linear unsaturated hydrocarbon group, an ether group, or an aryl group; and $R_2$ and $R_3$ independently have a structure of:

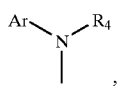

in which Ar is selected from the group consisting of:

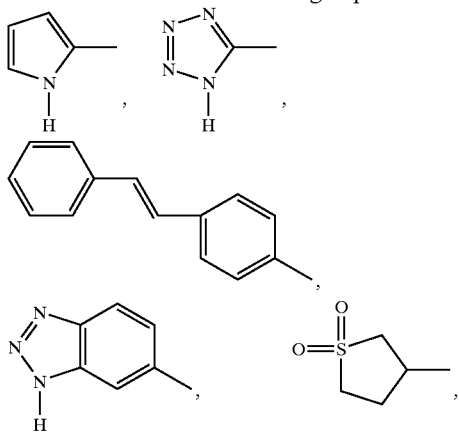

-continued

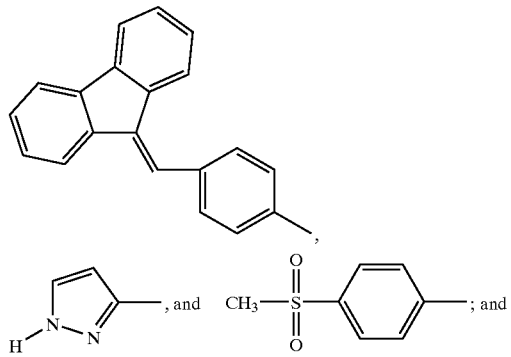

$R_4$ is a hydrogen or an aromatic group.

18. The charge transport compound according to claim 17 wherein $R_2$ and $R_3$ have the same structure.

19. The charge transport compound according to claim 17 wherein $R_2$ and $R_3$ have a different structure from each other.

20. A charge transport compound according to claim 17 wherein said charge transport compound comprises:

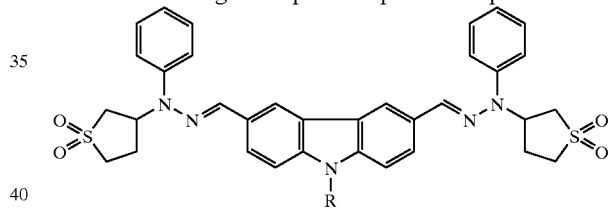

where R is hydrogen, a branched or linear alkyl group, a branched or linear unsaturated hydrocarbon group, an ether group, or an aryl group.

21. A charge transport compound according to claim 17 wherein said charge transport compound comprises:

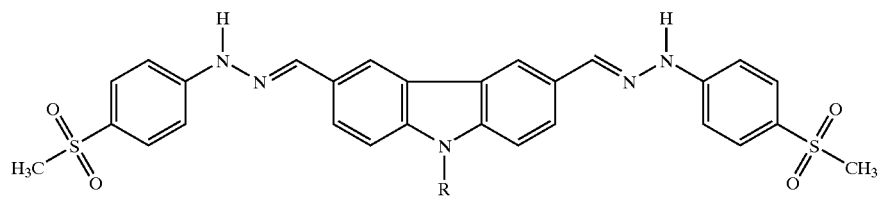

where R is hydrogen, a branched or linear alkyl group, a branched or linear unsaturated hydrocarbon group, an ether group, or an aryl group.

* * * * *